United States Patent [19]

Vennos

[11] 3,966,439
[45] June 29, 1976

[54] FLUID SAMPLING DEVICE

[76] Inventor: Spyros-Lysander N. Vennos, 4003 Milldale Court, Phoenix, Md. 21131

[22] Filed: Nov. 11, 1974

[21] Appl. No.: 522,904

[52] U.S. Cl. .................................. 55/270; 55/417; 55/485; 55/487; 55/501; 55/320; 55/503; 55/504; 55/DIG. 31; 210/136; 210/314; 210/356; 73/28; 73/421.5 R
[51] Int. Cl.² .................................. B01D 53/30
[58] Field of Search ............. 55/270, 417, 420, 485, 55/486, 487, 490, 495, 501, 502, 503, 504, 505, 509, 510, 511, DIG. 31, 494, 364, 320; 73/432 PS, 28, 421.5 A, 421.5 R; 210/136, 314, 356

[56] References Cited
UNITED STATES PATENTS

| | | | |
|---|---|---|---|
| 1,026,371 | 5/1912 | Smith .............................. | 55/509 X |
| 1,191,628 | 7/1916 | Trinks .............................. | 210/136 |
| 1,897,572 | 2/1933 | Cornell, Jr. ..................... | 210/136 X |
| 1,899,030 | 2/1933 | Gruman ........................... | 55/417 X |
| 2,225,990 | 12/1940 | Henry ............................. | 55/509 X |
| 2,419,664 | 4/1947 | Tabbert .......................... | 55/509 X |
| 3,015,228 | 1/1962 | Shuttleworth et al. ........... | 55/502 X |
| 3,350,979 | 11/1967 | Detweiler ........................ | 55/270 X |
| 3,422,679 | 1/1969 | McGowan et al. ............... | 55/270 X |
| 3,686,835 | 8/1972 | Strange et al. ................... | 55/270 |
| 3,782,083 | 1/1974 | Rosenberg ....................... | 55/501 X |

Primary Examiner—Frank W. Lutter
Assistant Examiner—David L. Lacey
Attorney, Agent, or Firm—Joseph P. Nigon

[57] ABSTRACT

A gaseous or liquid sampling collection unit designed to prevent loss of any of the matter collected and designed to prevent the accidental or intentional loss of all or part of the amount of matter collected, consisting of a filter capsule comprising a shield, and a filter, a two piece cassette containing said capsule consisting of an upper member and a close fitting lower member wherein the capsule is positioned between the upper and lower members of said cassette, the upper member of said cassette containing a valving arrangement permitting a unidirectional flow and, a tamper proofing plate preventing the accidental or intentional interference with the collection function.

9 Claims, 24 Drawing Figures

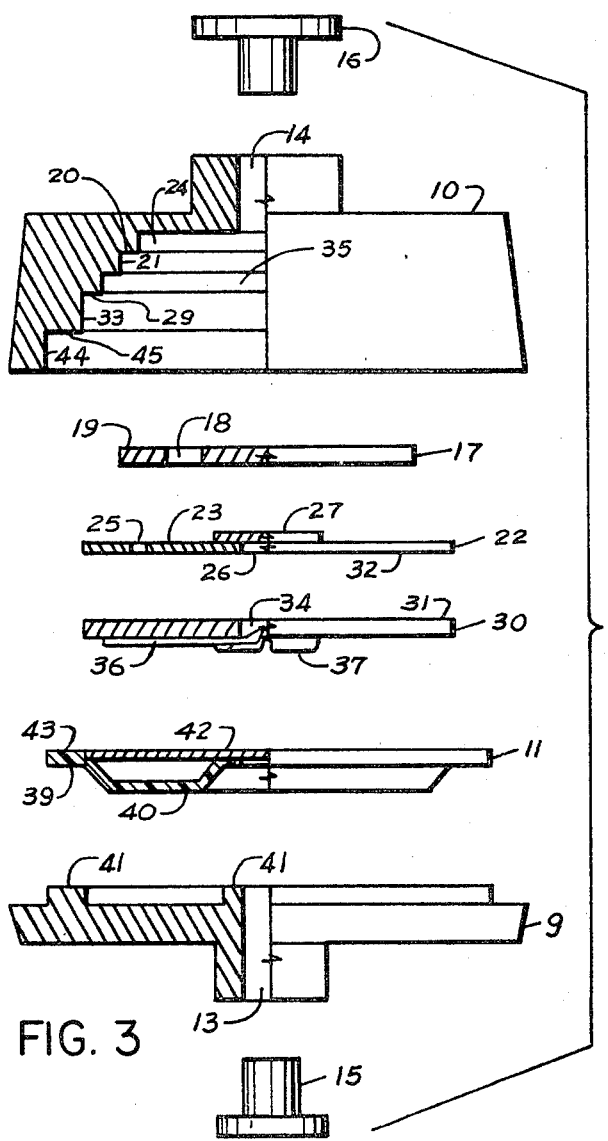
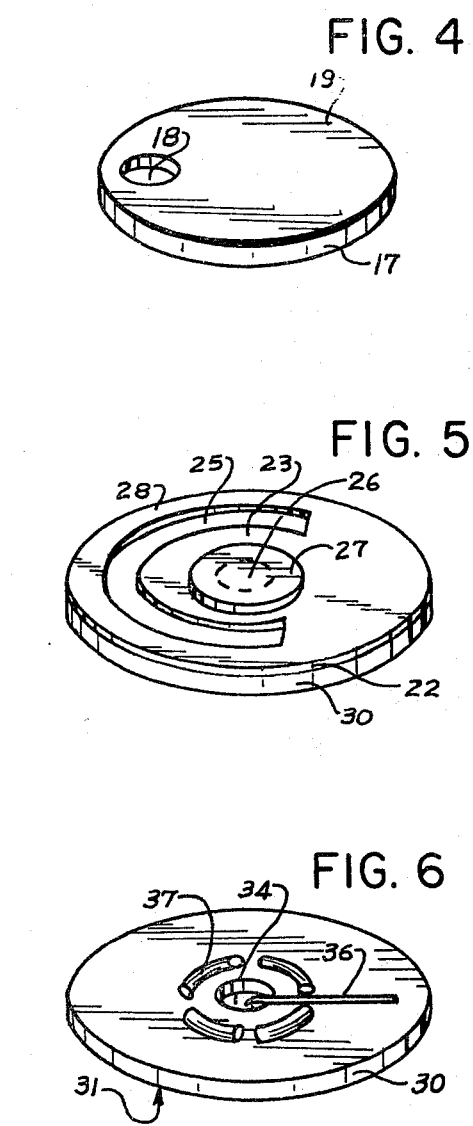

FLUID SAMPLING DEVICE

BACKGROUND OF THE INVENTION

There is a considerable demand for devices designed to sample air in factories, power plants, mines, etc., to determine the quantity of dust in the air at any one time. The quantity of fine dust particles (5 microns and below) is of particular interest since these particles are carried into the lungs during respiration. The air sampling devices consist of a pump, generally powered by a battery, a separator for removing the larger particles and a filter unit for collecting the dust particles less than 5 microns in size. The filter unit — a capsule, — is weighed before exposure to contamination for a definite period of time and is weighed again at the end of the air sampling period.

One of the shortcomings of the prior art devices is the failure to provide means of assuring that all of the particulate matter collected during sampling is present when the filter unit is weighed to determine the quantity of dust per cubic meter of air. Another shortcoming of the prior art devices is the failure to provide means for preventing the accidental or intentional loss (tampering) of the amount of matter collected. Still another shortcoming is the absence in the market of an ultra-light weight filter unit whereby higher weighing accuracies may be obtained.

Federal regulations require that the filter be made of a non-hygroscopic material and that the weight of the removable filter unit not exceed 5 grams, and that it be pre-weighed by the manufacturer with an accuracy of plus or minus 0.1 milligrams.

One of the objects of the invention is to provide a filter unit that complies with the above-mentioned Federal Specifications.

It is another object of the invention to provide a portable filter unit that is designed to preserve the physical integrity and purity of the filter capsule prior to its exposure to contamination monitoring.

It is another object of the invention to provide a portable filter unit that is designed to prevent any loss of the matter collected by the filter capsule during or after exposure to contamination monitoring.

It is another object of the invention to provide a portable filter unit that is designed to preserve the physical integrity of the filter capsule after its exposure to contamination.

It is another object of the invenion to provide a portable filter unit designed to prevent tampering with the collection process prior, during or after exposure of the filter capsule to contamination monitoring.

It is another object of the invention to provide a portable filter unit designed to provide positive evidence that tampering with the unit was attempted.

It is another object of this invention to provide a filter capsule unit having a total weight of less than five grams so that the amount of matter collected can be accurately determined.

It is another object of the invention to provide an ultralight weight all-filter capsule so that increased accuracy in weighing may be achieved.

DESCRIPTION OF THE DRAWINGS

FIG. 1 is a perspective view of the unit.

FIG. 2 is a cross-sectional view taken along the line 1—1 of FIG. 1.

FIG. 3 is an exploded sectional view of the unit.

FIG. 4 is a perspective view of the protective plate positioned in the exit end of the cassette and designed to preserve the physical integrity of the valve structure and to prevent accidental or intentional interference with the collection function.

FIG. 5 is a perspective view of the valve structure positioned in the exit end of the cassette and held in position by the retaining plate shown in FIG. 6.

FIG. 6 is a perspective view of the valve retaining plate and valve bursting mechanism positioned in the upper part of the cassette.

FIG. 20 is a cross sectional view of a modification of the entry part of the cassette compatible with ultra-light weight capsule designs.

Referring to FIGS. 1 and 2: A cassette is formed in two parts, a lower part 9 and an upper part 10 which are designed to be fitted together in a close friction fit that can be easily separated. These parts are preferably made from commercially available plastics such as high density polyethylene, for example. To effect an impervious seal between the two parts 9 and 10 holding the filter capsule 11 a tape 12 may be wrapped or shrunk around the cassette. The filter capsule 11 is positioned in the cassette in a manner such that it can be easily removed and replaced.

Referring to FIGS. 2 and 3: The two parts 9 and 10 of the cassette are provided with an inlet port 13 and an outlet port 14 respectively. Removable and replaceable end caps 15 and 16 are designed to cap these parts preserving the purity and physical integrity of the capsule 11 prior and after exposure to contamination monitoring.

Referring to FIGS. 2, 3, 4 and 5: A protective plate 17 bearing one or more through apertures 18 is an integral part of the upper part 10 of the cassette, a portion of its outer periphery 19 is seated against shoulder 20 while, its periphery or portion thereof is engaged against surfaces 21 and/or 20 of the upper part 10 of the cassette. Aperture 18 is so situated as to prevent accidental or intentional interference with valve structure 22. For example, if valve 23 is centrally located, opening 18 must be in an off center position so that aperture 18 and valve 23 are not in direct straight line relationship to each other. Hollow space 24 situated at the exit side of protective plate 17 is essential in the operation of the unit.

Referring to FIGS. 2, 3, and 5: Valve structure 22 is composed of a thin non-hygroscopic material bearing a through cut-out portion 25 resulting in a flapper valve 23. Flapper valve 23 bears a through aperture 26 covered with a thin impervious burstable membrane 27 integrally attached to the flapper valve via adhesive or heat seal means, for example. Alternatively, the thin burstable membrane 27 may be absent if instead of the through aperture 26, the flapper valve 23 is scored to enhance bursting.

Referring to FIGS. 2, 3, 5 and 6: Valve structure 22 is seated along its outer periphery 28 against shoulder 29 of the upper part 10 of the cassette and held in position by retaining plate 30 registering throughout its surface 31 against surface 32 of the valve structure. Retaining plate 30 throughout its periphery engages surface 33 of the upper part 10 of the cassette forming a seal. Non-exclusive engagement examples include friction fit and heat sealing. Retaining plate 30 bears a through aperture 34 corresponding to aperture 26 of the valve structure 22. The combined structure of retaining plate 30 and valve structure 22; an integral composite of the upper part of the cassette; permit a unidirectional direction of flow from inlet port 13 to exit port 14 and prevent any flow in the reverse direction via the unidirectional function of the flapper valve 23. Hollow space 35 situated on the exit side of the valve structure 22 is essential in the operation of the valve. In the embodiment shown in FIG. 5, flapper valve 23 is moved away from the surface 31 of the retaining plate 30. When the flow is cut off, the flapper valve returns to its original position as shown in FIGS. 3 and 5. The fluid flows through aperture 34 of the plate 30 discussed above. The flapper valve return to its original position may be assisted through resilient means located in cavity 35 of the cassette. When back pressure (reverse flow) is applied to the unit, membrane 27 bursts providing evidence of tampering with the unit. Bursting membrane 27 may be assisted through sharp means for example, pin 36, integrally situated on the inlet side of the retaining plate 30, its point pointing toward membrane 27. Protrusions 37 are essential in maintaining the billowing filter supports of the filter capsule 11 — discussed at length below — at a positive distance off the inlet main surface of the retaining plate 30.

Referring to FIGS. 7 and 8: Another embodiment of the retaining plate 30 is shown in FIGS. 7 and 8. This structure combines flapper valve 23, hinged at point 38 — and burstable membrane 27 in one structure as shown in FIGS. 7 and 8. The function of this unit is substantially the same as described above.

Referring to FIGS. 2 and 3: Filter capsule 11 is formed of a light weight metal or a thin plastic and consists of a holder 39 optionally formed with one or more annular reinforcing ribs 40 to provide rigidity to the capsule. Filter capsule 11 conforms snugly against the conformation of the protruding part 41 of the lower or inlet part 9 of the cassette. A filter-unit 42 is an integral part of the capsule 11 and is made up of one or more semi-permeable filter units discussed at length in connection with FIGS. 9 through 20. The capsule is designed so that the edges at the periphery of the filter unit are secured in the capsule by a crimping flange 43 surrounding the filter unit as is shown particularly well in FIGS. 9 through 20. Non-exclusively heat sealing or cementing may be also employed.

Figure 21:
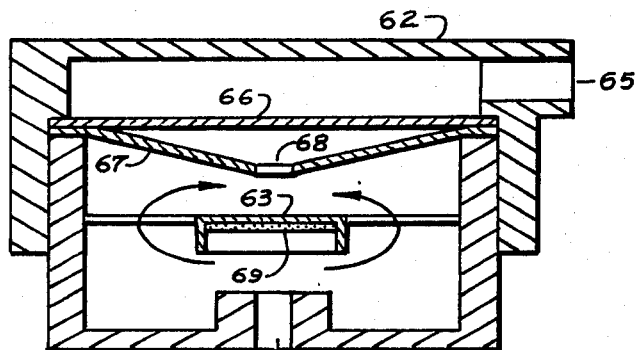
FIG. 21 is a cross sectional view of a U.S. Bureau of Mines device titled "Impactor Sampling Head."

The capsule 11 is inserted in the upper part 10 of the cassette following the sequential insertion of protective plate 17, valve structure 22 and retaining plate 30 as discussed above in detail. The filter capsule 11 in place, the lower or inlet part of the cassette — more particularly the outer annular area of protrusion 41 — is pressed into flange 44 of the upper or exit part 10 of the cassette forcing capsule 11 against shoulder 45 registering crimping flange 43 against said shoulder and providing a leakproof seal. Because of the necessity of easy removal of the capsule from the cassette employing an adhesive, pressure sensitive or a heat shrunk tape 12 may be necessary to provide assurance of a leakproof seal at the junction between the upper and lower parts of the cassette as well as between capsule and cassette halves.

In operation of the device, once a leakproof seal is secured, fluid will enter the device at port 13 and exit at port 14. Any solid contaminant matter (filtrate) will collect on the semi-permeable filter enclosed and held by the filter capsule 11. The filter capsule can be easily removed by separating inlet 9 and outlet 10 parts of the cassette.

On essential feature of the device resides in the protective plate 17 shown in FIGS. 2, 3, and 4 and discussed at length above. Another essential feature resides in the valved structure composite shown in FIG. 5 and also discussed at length above. Still another essential feature of the device resides in the design of the filter capsule 11 shown in FIGS. 2, 3 and 9 through 20 and discussed below.

Figure 9:
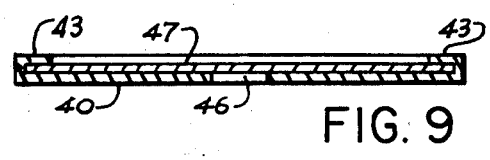

Referring to FIGS. 2, 3 and 9 through 20; The essential feature of the filter capsule unit is shown particularly well in FIGS. 9 and 10. As fluid enters the capsule through aperture 46 the filter 47 billows into cavity 8 of the cassette and the particulate matter moves as shown by the arrows in FIG. 10. When the fluid flow ceases, the filter returns to its original position as shown in FIG. 9 leaving the particulate matter entrained into the filter and held sandwiched between filter 47 and capsule shield 40 in areas 48. The return of the filter 47 to its original position may be assisted through resilient means located in cavity 8 of the cassette.

Figure 11:
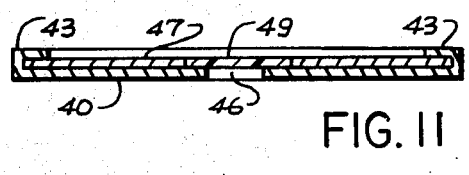
Figure 12:
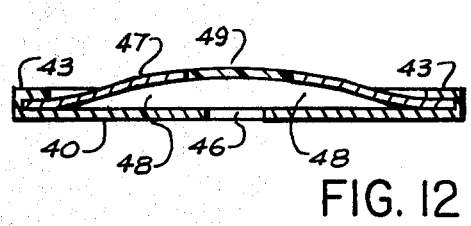

FIG. 11 shows a capsule structure similar to the structure of FIG. 9 except that filter 47 was rendered impermeable over an area 49 covering the corresponding area of aperture 46. FIG. 12 shows the capsule under flow conditions. When the fluid flow ceases the filter returns to its original position as shown in FIG. 11 trapping and holding any particulate matter collected sandwiching it between filter 47 and capsule shield 40 in areas designated 48 and securing the integrity of the sample collected.

Figure 13:
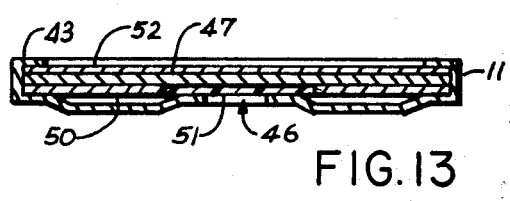
FIGS. 9 through 13 are cross sectional views of the filter capsule unit showing various modifications thereof.

FIG. 13 shows an embodiment of the capsule shown in FIG. 11 in which the filter 47 is protected by a semipermeable pre-filter element 50 which was rendered impermeable over an area 51 covering and corresponding to the aperture 46 and a second semipermeable post-filter support 52 providing a support for the filter 47. Relative to the size of the particulate matter sampled it is essential that element 50 be relatively more permeable than filter 47.

Figure 14:
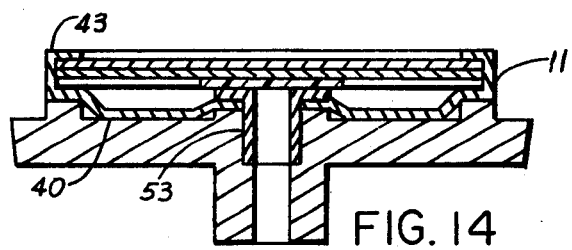
FIGS. 14 and 15 are cross sectional views of two modifications of the inlet portion of the cassette.

FIG. 14 shows an embodiment in which the filter capsule 11 has a protrusion 53 integral therewith. The filter units shown are as shown and as discussed in FIG. 13.

Figure 15:
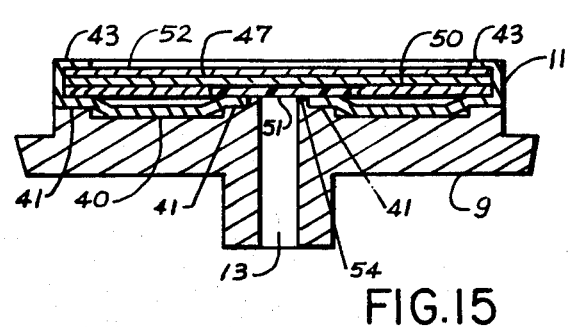

FIG. 15 shows an embodiment of the lower or inlet part of 9 of the cassette in which the capsule side of the inlet port 13 in addition to protrusion 41 discussed above has a further protrusion 54 in contact with the impermeable section of semi-permeable element 50. The contact is maintained at all times except when flow is established at which condition the composite three ply filter structure shown will billow away from protrusion 54. When the flow ceases, the filter composite returns to its orginal position entrapping the collected particulate matter.

Figure 16:
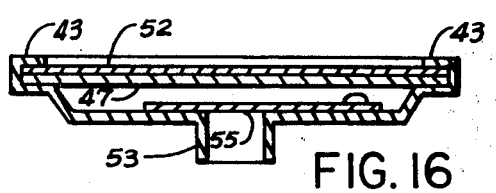
FIG. 16 is a cross sectional view of a modification of the filter capsule unit.

FIG. 16 shows an embodiment of the device wherein the capsule 11 has the protrusion 53 and is also equipped with a flapper valve 55 to assure that all of the particulate matter is entrapped within the capsule. Flapper valve 55 may be assisted by resilient means in returning to its original position.

As discussed above, federal regulations require that the filter be made of a non-hygroscopic material and that the weight of the removable filter capsule unit not exceed 5 grams and that it be pre-weighed by the manufacturer within one tenth of a milligram. Therefore, when the particulate sample collected is very small and to increase the weighing accuracy beyond the federal regulation requirements, it is advantageous to have a collecting filter capsule weighing as little as possible. FIGS. 16 through 20 show embodiments of filter capsule 11 designed to weigh as little as possible.

Figure 17:
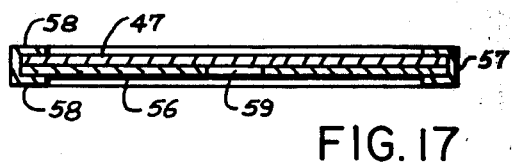
FIGS. 17 through 20 are cross sectional views of modifications of the filter capsule unit resulting in an ultra-light weight unit.

The essential feature of this embodiment is shown particularly well in FIG. 17. The essential elements of the filter capsule are at least two semi-permeable membranes 47 and 56 held together at their periphery by means 57 composed of a lightweight metal or thin plastic crimped on both sides by flanges 58. Alternatively and nonexclusively elements 47 and 56 may be held together at their periphery through heat sealing, cement, etc. resulting in an all filter ultra-light weight capsule.

Figure 18:
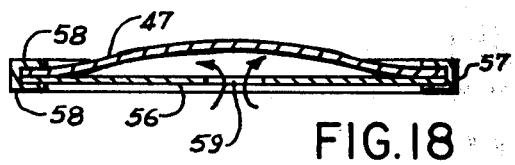
Figure 10:
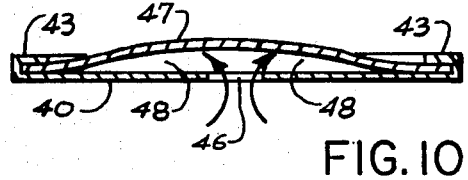

Filter element 47 is the element capturing the particulate matter. Semi-permeable element 56 bears an aperture 59 and may or may not be made of the same material as element 47. It is esssential that element 56 be at least as porous as element 47, and preferably less porous so that, the captured material may be retained within the capsule. FIG. 18 shows filter element 47 billowing into cavity 8 (see FIG. 2) under fluid pressure and as discussed in FIGS. 10 and 12. When the fluid is cut-off filter element 47 returns to its original position entrapping the collected material sandwiching it between the elements 47 and 56. Resilient means located in cavity 8 may assist filter elements to return to their original position.

Figure 19:
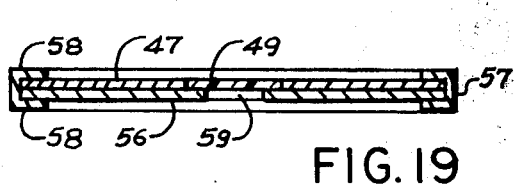

FIG. 19 shows an embodiment of an ultra-light weight filter capsule in which filter element 47 was rendered impervious over an area 49 corresponding and covering aperture 59 and designed to capture and entrap all the collected material sandwiching it between said elements 47 and 56.

Figure 20:
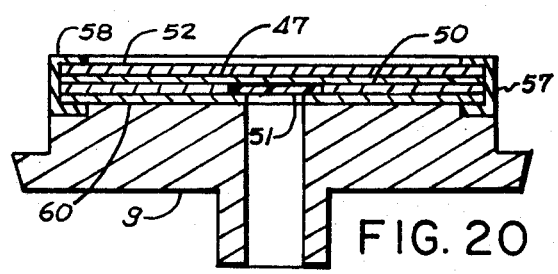

FIG. 20 shows an embodiment of an ultra-light weight filter capsule as well as an embodiment of the lower part or inlet part 9 of the cassette registering and conforming to the configuration of the ultra-light weight capsule. The capsule embodiment shows a four ply filter composite consisting of filter 47, pre-filter support 60, post filter support 52 and a semi-permeable element 50 rendered impermeable over area 51.

FIG. 21 shows a cassette designed by the U.S. Bureau of Mines titled "Impactor Sampling Head." The cassette as shown in FIG. 21 is not part of this invention but it is described in detail in publications by the U.S. Bureau of Mines. Since this structure is not part of this invention it is included and it is described briefly to demonstrate an additional versatility and a direct application of the invention claimed herein. Very briefly the U.S. Bureau of Mines cassette consists of two parts, a lower or inlet part 61 and an upper or exit part 62 fitted together in a close fit. An impactor plate 63 is positioned inside the lower part 61 impeding the flow entering inlet aperture 64 located in the lower part 61 and exiting through exit aperture 65 located in the upper part 62. Filter 66 preceeded by conical protective shield 67 bearing an aperture 68 are edge-peripherally and impermeably held together by the close fit between lower part 61 and upper part 62. Adhesive means 69 covering the impactor plate side facing the inlet port 64 selectively arrest particulate matter entering the cassette, allowing the remaining particles to proceed past the impactor plate 63 — as shown by the arrows — subsequently being captured by filter 66.

The shortcomings of this device substantially parallel those discussed earlier in detail. Most prominently and non-exclusively, it is the failure to provide means of assuring that all of the particulate matter collected during sampling is present when the filter unit is weighed. Also prominent is the ease of loss of particulate matter by applying a reverse flow as discussed earlier in detail.

Figure 22:
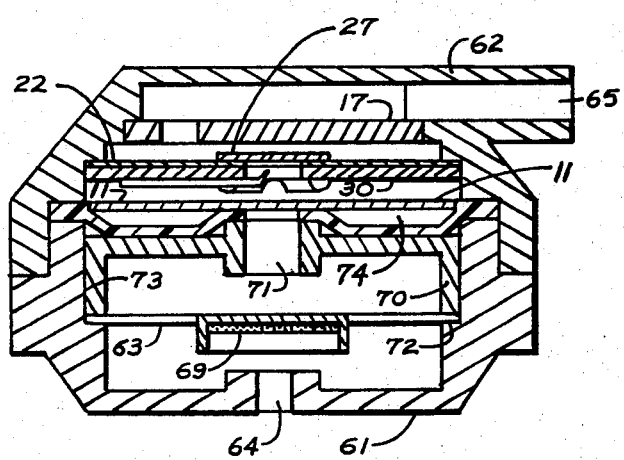
FIGS. 22, 23 and 24 are cross sectional views of improved embodiments of this invention relative to the U.S. Bureau of Mines device, embodying the capsule of this present invention.
Figure 24:
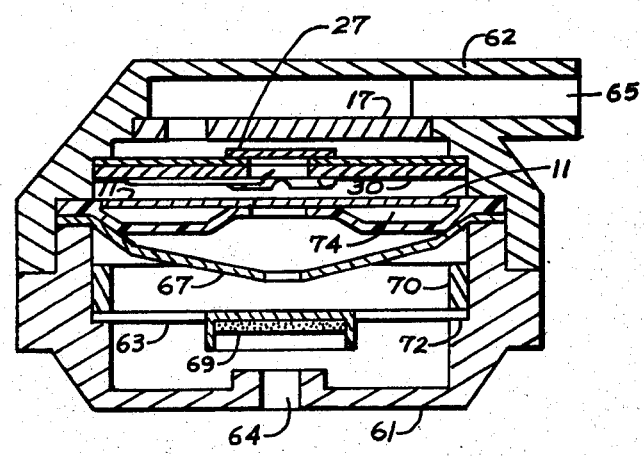
Figure 23:
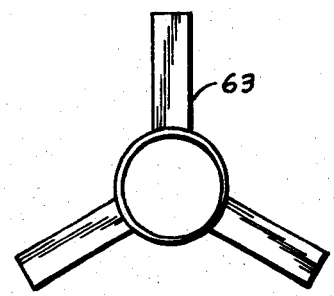
Figure 7:
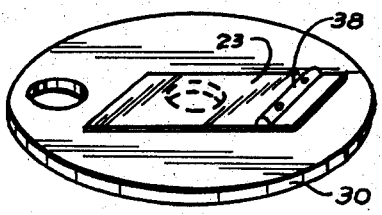
FIGS. 7 and 8 are perspective views of an alternate valved structure positioned in the upper part of the cassette.
Figure 8:
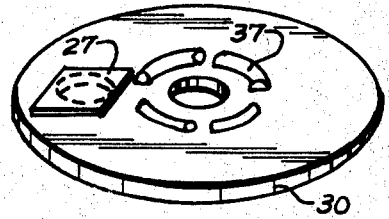

FIGS. 22 and 24 are embodiments of this invention resulting in an improved version of the U.S. Bureau of Mines "Impactor Sampling Head" alleviating all the shortcomings discussed above in detail. The embodiment shown in FIG. 22 differs substantially from the U.S. Bureau of Mines version. The lower or inlet part 61 in addition to impactor plate 63 contains element 70 — bearing aperture 71 — located on the downstream side of impactor plate 63 and performing a triple function. First, it retains impactor plate 63 (see FIG. 23) forcing it against shoulder 72 imperviously engaging lower part 61 along surface 73; second, it protects the exterior of capsule 11 from impinging particles and thirdly, it substantially conforms — on its exit side — to the configuration of capsule 11 occupying space 74. Space 74 may be occupied by any one of the filter capsules discussed with reference to FIGS. 2, 3 and 9 through 20 and described in coordination with appropriate exit side configurations of element 70. In addition, upper or exit part 62 contains plate 30, valving structure 22 and 27 and tamperproofing plate 17 described in detail in FIGS. 4 through 8, said elements totally absent in the U.S. Bureau of Mines design shown in FIG. 21.

The embodiment shown in FIG. 24 is similar to that shown in FIG. 22 differing in two aspects. First, element 70 is reduced to a retaining cylindrical shell. Second, protective shield 67 (see FIGS. 21 and 24) — a distinctly separate and readily separable element relative to capsule 11 — is imperviously held at its peripheral edge in registry with the peripheral edge of capsule 11 by lower part 61 and upper part 62.

What is claimed is:

1. A sample collection unit comprising in combination a hollow two piece cassette having a removable bottom member having an inlet port therein, a top member frictionally and imperviously engaging said bottom member and containing a valving structure means permitting unidirectional flow from said inlet port to said outlet port said top member having an outlet port therein, a filter capsule removably positioned in said cassette between said top and bottom members said filter capsule comprising at least two parts, one of said parts facing said inlet port of said cassette and consisting of a nonhygroscopic impervious shield having an aperture therein in registry with the inlet port of said removable bottom member, another of said parts comprising a filter mounted adjacent to and touching said shield in a region of the shield surrounding said aperture, the mounting of said filter with said shield causing a portion of its surface area to separate from said shield during flow conditions and to return to its original position when flow ceases, and means engaging the peripheral edge of said capsule to hold said capsule between the top and bottom members of said cassette.

2. The sample collection unit according to claim 1 wherein a portion of said filter unit is impervious in the area adjacent to the aperture of said shield, so that any particles entering said capsule are moved to its periphery during flow and are held between said shield and said filter when flow is discontinued.

3. The sample collection unit according to claim 1 wherein said shield is bent inwardly in the area surrounding said aperture and said inwardly bent portion contacts said filter at all times except during flow.

4. The sample collection unit according to claim 1 wherein said valve means comprises a cover having a free end that is hingedly positioned over the aperture of said shield and said filter, said free end of said cover moving away from said shield during flow, and returning to its original position when flow is discontinued.

5. A sample collection unit according to claim 1 wherein said filter is sandwiched between an upper pervious support and a lower pervious support.

6. The sample collection unit according to claim 1 wherein said filter is sandwiched between an upper pervious support and a lower pervious support, and a portion of said filter is impervious in the area of said filter touching the aperture in said shield, so that any particles entering said capsule are moved to its periphery during flow and are held between said shield and said filter when flow is discontinued.

7. A sample collection unit according to claim 1 wherein said top member of said cassette contains a tamper proofing plate positioned some distance away from the outlet port of said cassette and above said valve means, said plate having an aperture, one side of said plate facing the outlet port of said top member, and engaged frictionally over part of its periphery to said cassette, said plate aperture positioned in a manner such that its location prevents accidental or intentional interference with elements positioned on the side of said plate opposite to the one facing the outlet port of said cassette.

8. In a fluid sample collection unit comprising a hollow two piece cassette, a lower member having an inlet port and an annular shoulder therein, a close fitting top member having an outlet port, an impactor plate retained in said lower member, said plate having a surface in alignment with the axis of said lower member inlet port, said surface facing said inlet port covered with adhesive, the improvement comprising the addition of four elements, said first element comprising a first aperture bearing retaining plate engaging said lower member along its interior surface and retaining said impactor plate against said shoulder and positioning said impactor plate a definite distance away from said inlet port, a second element comprising a removably positioned filter capsule located downstream of said first aperture bearing retaining plate and including a filter and a reinforcing member having an aperture in registry with the aperture of said first element, said filter capsule held between said lower and top members of said cassette, a third element comprising a valve means located downstream of said capsule for allowing one-way fluid flow from said inlet port to said outlet port, said valve means comprising a second aperture bearing retaining plate, a bursting mechanism, and a one way valve for controlling flow through said second retaining plate aperture, and a fourth element comprising an apertured tamper-proofing plate located downstream of said valve means, said casette allowing one-way flow of fluid entering said inlet port, impinging upon said impactor plate, flowing around said impactor plate, entering said first element aperture, entering said capsule, flowing through said valve means, flowing through said tamperproofing plate, and exiting through said outlet port, particulate matter carried by said flow being captured within said capsule.

9. In a fluid sample collection unit comprising a hollow two piece cassette, a lower member having an inlet port and an annular shoulder therein, a close fitting top member having an outlet port therein, an impactor plate retained in said lower member of said cassette, said impactor plate having a surface in alignment with the inlet port of said lower member, said impactor plate surface facing said inlet port covered with adhesive means, the improvement comprising the addition of five elements, said first element comprising a retaining cylindrical shell engaging said lower member along its interior surface and retaining said impactor plate against said shoulder positioning said impactor plate at a definite distance away from said inlet port, a second element located downstream of said first element and comprising a protective shield imperviously held at its peripheral edge of said lower and top members of said cassette, said shield having an aperture, a third element located downstream of said second element and comprising a removably positioned filter capsule held in registry with the peripheral edge of said shield between said lower and top members of said cassette, said third element comprising an aperture bearing structure and a filter element, a fourth element located downstream of said third element and comprising a valve means for allowing one-way flow, said valve means including an apertured plate, a flap, and a bursting mechanism, and a fifth element located downstream of said fourth element and comprising a tamperproofing plate having an aperture, said cassette allowing the unidirectional establishment of flow entering said inlet port, said flow impinging upon said impactor plate, flowing around said impactor plate, entering said capsule, flowing through said fourth element valve means, flowing through the aperture in said tamperproofing plate and exiting through said outlet port, particulate matter carried by said flow being captured within said capsule.

* * * * *